(12) United States Patent
Huang et al.

(10) Patent No.: US 8,153,607 B2
(45) Date of Patent: Apr. 10, 2012

(54) TRANSCRIPTION FACTOR DECOYS AND USE THEREOF

(75) Inventors: Kuang-Tse Huang, Minhsiung Township (TW); Jian-En Lin, Minhsiung Township (TW)

(73) Assignee: National Chung Cheng University, Chiayi County (TW)

( * ) Notice: Subject to any disclaimer, the term of this patent is extended or adjusted under 35 U.S.C. 154(b) by 16 days.

(21) Appl. No.: 12/626,969

(22) Filed: Nov. 30, 2009

(65) Prior Publication Data

US 2011/0054010 A1 Mar. 3, 2011

(30) Foreign Application Priority Data

Aug. 27, 2009 (TW) .............................. 98128771 A

(51) Int. Cl.
*A61K 31/70* (2006.01)
*C07H 21/04* (2006.01)
*C12Q 1/00* (2006.01)

(52) U.S. Cl. ........................................ 514/44; 536/24.1

(58) Field of Classification Search ........................ None
See application file for complete search history.

(56) References Cited

U.S. PATENT DOCUMENTS

| | | | | |
|---|---|---|---|---|
| 5,679,559 A * | 10/1997 | Kim et al. | ...................... | 435/458 |
| 7,186,556 B2 * | 3/2007 | Hecker et al. | .................. | 435/375 |
| 7,910,423 B2 * | 3/2011 | Ohara | ............................ | 438/199 |
| 2004/0191779 A1 * | 9/2004 | Zhang et al. | ....................... | 435/6 |

OTHER PUBLICATIONS

S. J. Streat, L. D. Plank, and G. L. Hill, World J. Surg., 24 (2000) 655-663.
C. Granja, C. Dias, A. Costa-Pereira, and A. Sarmento, Crit Care., 8 (2004) R91-R98.
W. A. Knaus, E. A. Draper, D. P. Wagner, and J. E. Zimmerman, Ann. Surg., 202 (1985) 685-693.
D. L. Hoyert, E. Arias, B. L. Smith, S. L. Murphy, and K. D. Kochanek, Natl. Vital Stat. Rep., 49 (2001) 1-113.
S. M. Dauphinee and A. Karsan, Lab Invest., 86 (2006) 9-22.
S. Yang, M. Zhou, D. J. Koo, I. H. Chaudry, and P. Wang, Am. J. Physiol., 277 (1999) H1036-H1044.
R. C. Bone, R. A. Balk, F. B. Cerra, R. P. Dellinger, A. M. Fein, W. A. Knaus, R. M. Schein, and W. J. Sibbald, The ACCP/SCCM Consensus Conference Committee. American College of Chest Physicians/Society of Critical Care Medicine, Chest., 101 (1992) 1644-1655.
A. P. Wheeler and G. R. Bernard, N. Engl. J. Med., 340 (1999) 207-214.
E. D. Papathanassoglou, J. A. Moynihan, and M. H. Ackerman, Crit Care Med., 28 (2000) 537-549.
H. Steller, Science., 267 (1995) 1445-1449.
R.Pfeiffer, Untersuchungen uber das Choleragift, Medical Microbiology and Immunology, 11 (1892) 393-412.
J. T. Rosenbaum, H. O. McDevitt, R. B. Guss, and P. R. Egbert, Nature., 286 (1980) 611-613.
M. Riewald, R. J. Petrovan, A. Donner, B. M. Mueller, and W. Ruf, Science., 296 (2002) 1880-1882.
V. S. Ossovskaya and N. W. Bunnett, Physiol Rev., 84 (2004) 579-621.
C. H. Woo and J. H. Kim, Rac G, Mol. Cells., 13 (2002) 470-475.
Y. Li, B. Du, J. Q. Pan, D. C. Chen, and D. W. Liu, J. Zhejiang. Univ Sci. B., 7 (2006) 899-905.
J. Vachtenheim, B. Sestakova, and Z. Tuhackova, Pigment Cell Res., 20 (2007) 41-51.
B. Mann, M. Gelos, A. Siedow, M. L. Hanski, A. Gratchev, M. Ilyas, W. F. Bodmer, M. P. Moyer, E. O. Riecken, H. J. Buhr, and C. Hanski, Proc. Natl. Acad. Sci. U. S. A., 96 (1999) 1603-1608.
S. M. Gardiner, P. A. Kemp, J. E. March, and T. Bennett, Br. J. Pharmacol., 116 (1995) 2005-2016.
G. R. Bernard, J.Vincent, P Laterre, S. P. LaRosa, J. Dhainaut, A. Lopez-Rodriguez, M.D., J. S. Steingrub, G. E. Garber, J. D. Helterbrand, E. W. Ely, and C. J. Fisher, N. Engl. J, Med., 344 (2001), 699-709.
C. J. Hinds, B. M. J., 323 (2001) 881-882.
A. Hecht, K. Vleminckx, M. P. Stemmler, F. van Roy, and R. Kemler, The EMBO Journal, 19 (2000) 1839-1850.
S.W. Kim, J Control Release (1998), 53: 175-182.

* cited by examiner

*Primary Examiner* — Quang Nguyen
(74) *Attorney, Agent, or Firm* — Frenkel & Associates, PC

(57) ABSTRACT

A pharmaceutical composition having a transcription factor decoy and a pharmaceutical acceptable carrier thereof is provided, wherein the transcription factor decoy is TCF decoy. A method for curing or preventing endotoxin-treated endothelial cells from apoptosis is provided. A method for treating or meliorating septic shock is also provided. The transcription factor decoy is effective on melioration of endothelial cell death after lipopolysaccharide challenge. Furthermore, the pharmaceutical composition is easy to be prepared, economic and has low immunogenicity.

2 Claims, 7 Drawing Sheets

SEQUENCE LISTING

<160> NUMBER OF SEQ ID NOS: 5

<210> SEQ ID NO 1
<211> LENGTH: 14
<212> TYPE: DNA
<213> ORGANISM: Artificial
<220> FEATURE:
<223> OTHER INFORMATION: P300 decoy

<400> SEQUENCE: 1
tgggggagtg caca                                                     14

<210> SEQ ID NO 2
<211> LENGTH: 14
<212> TYPE: DNA
<213> ORGANISM: Artificial
<220> FEATURE:
<223> OTHER INFORMATION: mismatch P300 decoy

<400> SEQUENCE: 2
gtggggaggt caca                                                     14

<210> SEQ ID NO 3
<211> LENGTH: 20
<212> TYPE: DNA
<213> ORGANISM: Artificial
<220> FEATURE:
<223> OTHER INFORMATION: TCF decoy (TCF-CyD1)

<400> SEQUENCE: 3
gggctttgat ctttgcttaa                                               20

<210> SEQ ID NO 4
<211> LENGTH: 20
<212> TYPE: DNA
<213> ORGANISM: Artificial
<220> FEATURE:
<223> OTHER INFORMATION: TCF decoy (TCF-Fra1)

<400> SEQUENCE: 4
agaatccctt tagctcagga                                               20

<210> SEQ ID NO 5
<211> LENGTH: 19
<212> TYPE: DNA
<213> ORGANISM: Artificial
<220> FEATURE:
<223> OTHER INFORMATION: mismatch TCF decoy

```
<400> SEQUENCE: 5
gggcttgtat cttgtctta                                                    19
```

TRANSCRIPTION FACTOR DECOYS AND USE THEREOF

BACKGROUND OF THE INVENTION

1. Field of the Invention

The present invention relates to transcription factor decoys for preventing cell apoptosis induced by endotoxin and use thereof, particularly to a DNA decoy for reducing cell apoptosis of endothelial cells induced by endotoxin. The present invention also relates to a pharmaceutical composition for curing or preventing cells from cell apoptosis induced by endotoxin, which comprises transcription factor decoy.

2. Description of the Prior Arts

Although progress and response of sepsis is becoming more predictable, there is still a need for effective therapy for sepsis (S. J. Streat, et al., *World J. Surg.*, 2000, 24: 655-663). The mortality of sepsis patients is up to 26% in intensive care unit (ICU) and even up to 34% in high risk groups (C. Granja, et al., *Crit. Care.*, 2004, 8: R91-R98). The symptom of sepsis includes shock, thrill, rapid breathing and heart rate and the like. Multiple organ failure is the major cause of high mortality, as high as 98%, in ICU (W. A. Knaus et al., *Ann. Surg.*, 1985, 202: 685-693). Since sepsis ranks as the twelfth leading cause of death (D. L. Hoyert, et al., *Natl. Vital Stat. Rep.*, 2001, 49: 1-113), development and improvement of therapy for sepsis is an urgent and important need.

Sepsis is a systemic inflammatory response (SIR) against bacterial infection (S. M. Dauphinee and A. Karsan, *Lab Invest.*, 2006, 86: 9-22). The underlying mechanism of sepsis resides in serial responses of host and immune system caused by entrance of pathogen into blood, resulting in hyperdynamic state with increased cardiac output in an early phase, hypodynamic state with decreased cardiac output in a late phase, and finally a reduction of systemic vascular resistance and dilation of peripheral vessels, leading to hypotension and organ ischemia, so called septic shock (S. Yang, et al., *Am. J. Physiol.*, 1999, 277: H1036-H1044). Since vasopressor is not effective against septic shock, sustained septic shock causes multiple organ dysfunction (MOD) and finally leads to multiple organ failure (MOF) and death (R. C. Bone, et al., *The ACCP/SCCM Consensus Conference Committee. American College of Chest Physicians/Society of Critical Care Medicine, Chest.*, 1992, 101: 1644-1655).

Recently, several studies have indicated that multiple organ failure induced by sepsis is caused by cell apoptosis (E. D. Papathanassoglou, et al., *Crit. Care Med.*, 2000, 28: 537-549). Cell apoptosis is confirmed to be a significant mechanism against pathogens (H. Steller, *Science.*, 1995, 267: 1445-1449). Sepsis is strongly associated with exogenous pathogen, bacterial endotoxin (S. M. Dauphinee and A. Karsan, *Lab Invest.*, 2006, 86: 9-22).

Bacterial endotoxin is a major component of cell wall of Gram-negative bacteria, composed of polysaccharide and lipid. Therefore, endotoxin is also called lipopolysaccharide (LPS) (R. Pfeiffer, Untersuchungen uber das Choleragift, *Medical Microbiology and Immunology*, 1892, 11: 393-412). Pathophysiological mechanism of LPS-induced endotoxsemia resides in LPS entering a human body and engaging with CD14 on cell membranes of immune cells to form a complex and stimulating macrophages, monocytes and T lymphocytes of host immune system through downstream signaling to produce cytokines and inflammatory precursors such as prostaglandin (S. M. Dauphinee and A. Karsan, supra.; J. T. Rosenbaum, et al., *Nature*, 1980, 286: 611-613), resulting in inflammation, hyperplasia and apoptosis and finally sepsis. Current clinical therapies for sepsis includes hemodynamic monitoring, fluid replacement, pathogen control, antibiotic therapy, airway management, monitoring of renal function, blood sugar control and prevention of complication (A. P. Wheeler and G. R. Bernard, *N. Engl. J. Med.*, 1999, 340: 207-214). All the above-mentioned monitoring and therapies are preventive and passive. No therapy exists that is immediately effective for severe sepsis or septic shock (S. J. Streat, et al., 2000, supra).

Only one drug for treating severe sepsis has been approved by the US Food and Drug Administration (FDA), activated protein C (APC). Clinical tests in 1960 sepsis patients with different sources of pathogens, ages, conditions and severity of organ dysfunction showed that activated protein C decreases 28-day mortality from 30.8% to 24.7%. (G. R. Bernard, et al., *N. Engl. J, Med.*, 2001, 344: 699-709). In another clinical test, 70% of sepsis patients who were over 60 years old were selected and comprised 386 people, 40% of the 70% sepsis patients, who were over 75 years old were subjected to APC treatment and the 28-day and 2-year mortality was monitored. APC treatment was found to have no side effects in patients at different ages (C. J. Hinds, B. M. J., 2001, 323: 881-882). Therefore, the FDA approved APC for treating sepsis in Nov. 21, 2001.

Activated protein C is physiologically obtained by activating protein C (PC). PC is a vitamin K-dependent protein C, which is synthesized in the liver and contains a light chain of 155 amino acids and a heavy chain of 304 amino acids linked by disulfide bonds. PC belongs to serine protease family PC is activated by binding to thrombin (T) and thrombomodulin (TM) known as T-TM mechanism, which is regulated by endothelial protein C receptor (EPCR). APC exerts anticoagulant activity through cutting and inhibiting coagulation cofactors F VIIIa and coagulation cofactors F Va.

Receptor of APC on endothelial cells has been identified as proteinase-activated receptor 1 (PAR1). When PC is activated to APC, PAR1 and endothelial protein C receptor will both be expressed after PAR1 is activated by APC. Serial anti-inflammatory reactions are aroused by PAR1, which include suppression of p53, modulation of Bax/Bcl-2 and decrease of Caspase 3 signaling. These result in inhibiting IL-1, IL-6 and TNF-α synthesis to avoid cell apoptosis.

PAR is G protein-coupled receptor, including 7 transmembrane domains, and belongs to a family consisting of PAR1, PAR2, PAR 3 and PAR4, wherein PAR1, PAR3 and PAR4 can be activated by thrombin; and PAR2 can only be activated by trypsin, tryptase, and coagulation cofactor VIIa and Xa. The difference between PAR1 and other G protein is that activation of PAR1 is irreversible. Therefore, activated PAR1 enters lysosomes instead of being recycled to membrane. Due to PAR1's unique characters, PAR1 plays an important role in APC pathway.

Although APC has been confirmed as having a therapeutic effect on sepsis, use of APC on treatment of sepsis still has disadvantages. For example, percentage of severe hemorrhage occurring in sepsis patients increases from 2% to 3.5% and half-life of APC in blood is only 1.6 hour (G. R. Bernard, et al., *N. Engl. J, Med.*, 2001, 344: 699-709). Collectively, in the field of the art there are no therapeutically effective pharmaceutical compositions or methods for treating sepsis. Accordingly, there is an urgent need for an effective and immediate novel therapy for sepsis.

To overcome the shortcomings, the present invention provides a composition and method for curing or preventing endotoxin-treated endothelial cells from apoptosis and also for treating sepsis to mitigate or obviate the aforementioned problems.

SUMMARY OF THE INVENTION

Given the aforementioned problems, the main objective of the present invention is to provide pharmaceutical compositions, methods for curing or preventing endotoxin-treated endothelial cells and for treating or alleviating sepsis and use thereof.

In one aspect, the present invention provides a transcription factor decoy, comprising an oligonucleotide consisting of a sequence which is selected from the group consisting of: GGGCTTTGATCTTTGCTTAA (SEQ ID NO: 3), AGAATCCCTTTAGCTCAGGA (SEQ ID NO: 4) and complementary sequences thereof.

In another aspect, the present invention provides a pharmaceutical composition comprising at least one transcription factor decoy and a pharmaceutically acceptable carrier thereof, wherein the at least one transcription factor decoy is TCF decoy.

Preferably, the TCF decoy is selected from the group consisting of: oligonucleotides comprising sequence of GGGCTTTGATCTTTGCTTAA (SEQ ID NO.: 3), AGAATCCCTTTAGCTCAGGA (SEQ ID NO.: 4) and complementary sequence and derivatives thereof.

In another aspect, the present invention also provides a method for curing endotoxin-treated endothelial cells from apoptosis, which comprises:

administrating a pharmaceutical composition as described above to endothelial cells stimulated by endotoxin, such that cell apoptosis of endothelial cells induced by endotoxin is decreased.

In another aspect, the present invention also provides a method for treating or alleviating sepsis, comprising: administrating a pharmaceutical composition to a patient with sepsis, wherein the pharmaceutical composition comprises at least one transcription factor decoy and a pharmaceutically acceptable carrier thereof, and the at least one transcription factor decoy is TCF decoy or P300 decoy.

Preferably, the transcription factor decoy is P300 oligonucleotide decoy or TCF oligonucleotide decoy.

More preferably, the transcription factor decoy is selected from the group consisting of: GGGCTTTGATCTTTGCTTAA (SEQ ID NO.: 3), AGAATCCCTTTAGCTCAGGA (SEQ ID NO.: 4), and complementary oligonucleotides and derivatives thereof.

In another aspect, the present invention provides a method for preparing a pharmaceutical composition for treating or alleviating sepsis, comprising: providing a transcription factor decoy and a pharmaceutically acceptable carrier thereof; and mixing the transcription factor decoy and the pharmaceutically acceptable carrier to form the pharmaceutical composition for treating or alleviating sepsis, wherein the transcription factor decoy is P300 decoy or TCF decoy.

Preferably, the TCF decoy in accordance with the present invention is TCF oligonucleotide decoy comprising a sequence of:

```
GGGCTTTGATCTTTGCTTAA        (SEQ ID NO.: 3)
or
AGAATCCCTTTAGCTCAGGA.       (SEQ ID NO.: 4)
```

More preferably, the pharmaceutically acceptable carrier in accordance with the present invention comprises palmitoyl poly-L-Lysine-low density lipoprotein (pal-P-L-Lys-LDL), which is obtained from mixing palmitoyl chloride and poly-L-Lysine at a ratio of about 1:1 by weight, wherein poly-L-Lysine provides positive charge to bind to negative charge of transcription factor decoy; and low density lipoprotein binds to low density lipoprotein receptor to induce potocytosis.

Preferably, the transcription decoy and the pharmaceutically acceptable carrier are mixed at a ratio of 1:0.5 by weight.

In another aspect, the present invention provides a method for curing or preventing endothelial cells treated with endotoxin from cell apoptosis, comprising: administrating a pharmaceutical composition in accordance with the present invention to endothelial cells stimulated by endotoxin, such that cell apoptosis of endothelial cells induced by endotoxin is decreased.

According to the present invention, the transcription factor decoy, particularly TCF oligonucleotide decoy, is proved to be able to alter expression of APC-associated genes, effective for curing endotoxin-treated endothelial cells from apoptosis and for treating or meliorating sepsis induced by bacterial infection. The TCF oligonucleotide decoy in accordance with the method for preparing the pharmaceutical composition for curing or preventing endotoxin-treated endothelial cells from apoptosis and for treating or meliorating sepsis is conveniently and economically produced. Moreover, the method for treating or meliorating sepsis in accordance with the present invention is economic and less immunogenic. Preferably, the pharmaceutical carrier in accordance with the present invention is pal-P-L-Lys-LDL, which contains low density protein capable of binding to low density protein receptor on cells to trigger potocytosis. Therefore, the transcription factor decoy in accordance with the present invention can be easily introduced into target cells.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
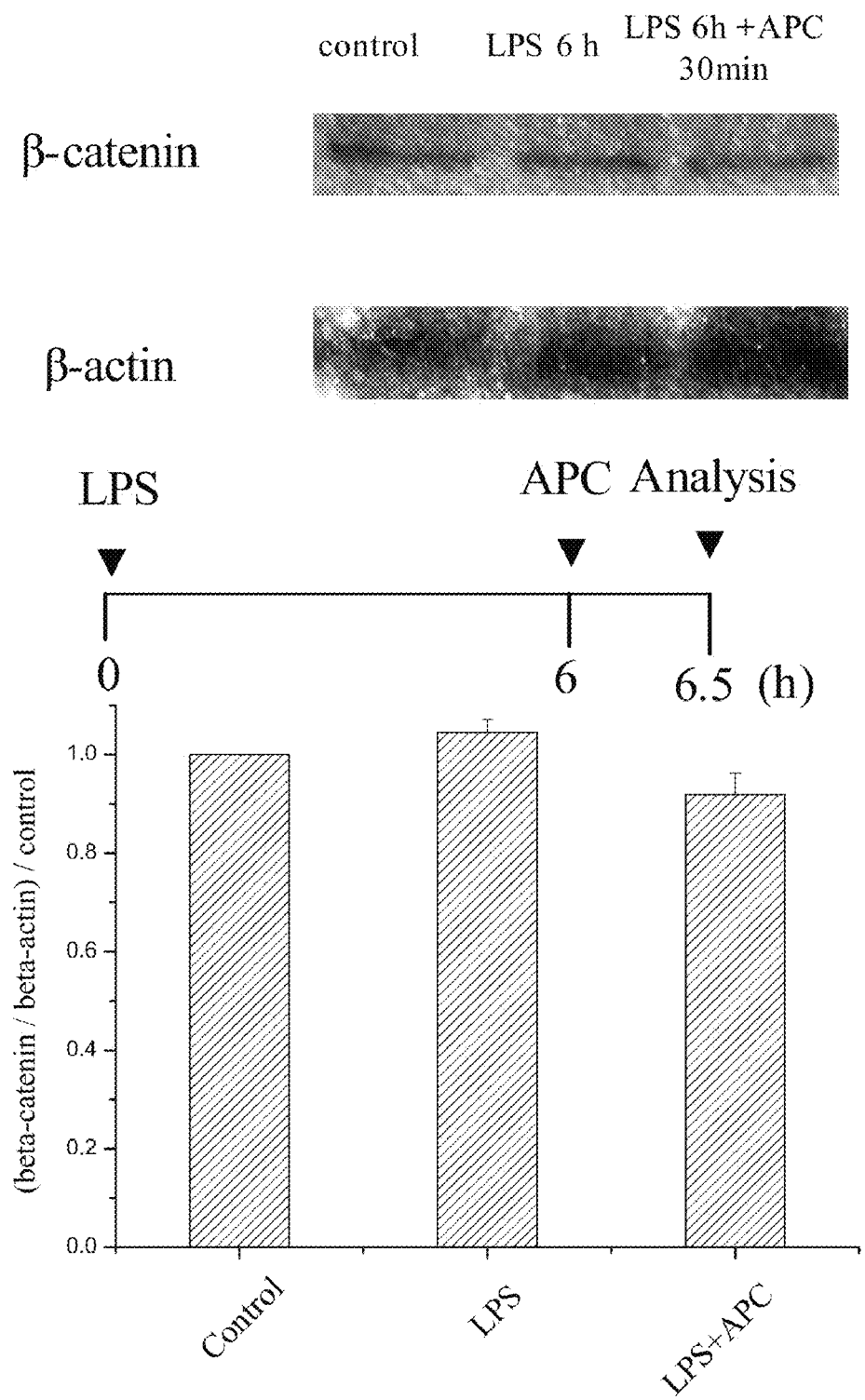
FIG. 1 illustrates effect of LPS and APC treatment on protein amount of intracellular β-catenin.

According to the present invention, the term "decoy" or "transcription factor decoy" refers to a compound including oligonucleotides or the derivative thereof capable of binding to TCF transcription factor. Once the decoy exists in cell nucleus, it will antagonize or bind to transcription factor, resulting in influencing expression of gene regulated by said transcription factor. The P300 is DNA and β-catenin binding protein, such as, but not limited to acetyltransferase, capable of altering chromatin structure and recruiting general transcription factors to facilitate gene transcription modulated by β-catenin (A. Hecht, *The EMBO Journal*, 2000, 19: 1839-1850).

The TCF is DNA and β-catenin binding protein. TCF alone can not exert its regulatory function (A. Hecht, 2000, *supra*).

Particularly, "P300 decoy" refers to a compound including nucleotides or the like antagonizing or binding to P300. More particularly, "P300 oligonucleotide decoy" refers to a polynucleotide antagonizing or binding to P300. Even more particularly, P300 DNA decoy refers to deoxyribonucleic acid antagonizing or binding to P300, and it is used for comparison.

"TCF decoy" refers to a compound including nucleotides or the derivative thereof antagonizing or binding to TCF. More particularly, "TCF oligonucleotide decoy" refers to a polynucleotide antagonizing or binding to TCF. Even more particularly, TCF DNA decoy refers to deoxyribonucleic acid antagonizing or binding to TCF.

According to the present invention, the transcription factor decoy includes: GGGCTTTGATCTTTGCTTAA (SEQ ID NO: 3), AGAATCCCTTTAGCTCAGGA (SEQ ID NO: 4) and complementary sequences thereof; their variant; compound including at least one thereof; and combination thereof.

The transcription factor decoy include a nucleic acid fragment, a modified nucleic acid, pseudonucleic acid having nucleotide sequence as described above and other derivatives as known in the art. Further, the transcription factor decoy includes mutant of oligonucleotides as described above. The described oligonucleotides may be double strain, circular or linear. The described mutant is any of the described oligonucleotides having mutation, substitution and insertion nucleic acid, wherein the mutant is capable of antagonizing or binding to TCF.

The modified nucleic acid includes those capable of resisting in vivo degradation or the like, such as oligonucleotide containing thiophophatediester bond, oligonucleotide with thiophophatediester substituted by methylphophate and the like.

According to the present invention, the decoy may be synthesized by any known preparation method in the art. For example, when the decoy is nucleic acid, which can be prepared by common method for synthesizing nucleic acid in the field of genetic engineering, including, by a DNA synthesizer. On the other hand, a portion of nucleic acid may be directly synthesized and further subjected to polymerase chain reaction (PCR) and cloning for amplification. Further, a desired nucleic acid may be obtained by restriction enzyme or ligase. For stabilizing intracellular nucleic acid, further chemical modification, such as alkylation, acylation, pegylation, or other similar reaction, to a basic group, glycosyl group or phosphorylated portion may be performed.

The pharmaceutical composition according to the present invention is any form capable of introducing the decoy as described above into cells of a target part or tissue.

The pharmaceutical composition according to the present invention is orally or parenterally administrated. Parenteral administration includes intraarterial, intramuscular, subcutaneous, intromedullary, into subarachnoid space, intraventricular, intravenous, intraperitoneal or intranasal administration.

The pharmaceutical composition according to the present invention comprises: at least one transcription factor decoy and pharmaceutical acceptable carrier thereof, wherein the transcription factor decoy is TCF decoy. The pharmaceutical composition is at any form suitable for gene transfer method, for example, but not be limited to liposome. The method for producing liposome is not limited to any particular method, only that the method makes liposome hold the transcription factor decoy, such as reversed phase evaporation, ether infusion method and surfactant method.

Preferably, the pharmaceutical composition is prepared by mixing the transcription factor decoy with pal-P-L-Lys-LDL.

According the present invention, the term "treating", "curing" or "preventing" as used hereby refers to patients or cells to be treated receive an effective amount of the pharmaceutical composition as mentioned above. Sepsis is confirmed relating to bacterial endotoxin. Therefore, in the following examples, bacterial endotoxin is used to simulate sepsis. The efficiency of sepsis therapy and control is evaluated by level of cell apoptosis. Besides, Gardiner et al. in 1995 disclosed nitric oxide is associated with vascular changes in sepsis (S. M. Gardiner, et al., *Br J. Pharmacol.*, 1995, 116: 2005-2016). Therefore, amount of released nitric oxide is also analyzed to determine efficiency of sepsis therapy and control.

In the following examples, analysis of regulatory region of APC-associated genes indicates that P300 binding site and TCF binding site of APC-associated gene is correlated to activation of APC-associated genes. DNA decoys are designed according to P300 binding site and TCF binding site. Viability of endothelial cells stimulated with LPS is increased by treatment of DNA decoy. P300 and TCF DNA decoys are confirmed to be effective to treat sepsis.

First, the applicant studies on expression of PAR1 activated genes in APC-treated endothelial cells. Using the obtained gene list to compare with TFSEARCH database provided online by Parallel Application TRC Laboratory, RWCP (Japan), the transcription factors related to the gene described above are found, as shown in Table 1. Only factors having scores higher than 80 are selected, resulting in 90 related genes, 40 of which contain at least one P300 binding site, 14 of which contain at least one CBP binding site, 10 of which contain at least one of both a P300 binding site and a CBP binding site, none of which contain a TCF binding site.

Comparing mRNA expression of the endothelial cells that are treated with APC and the control, it is found that average induction of the mRNA expression of 13 genes are over 2 times of their original. None of the genes contain a TCF binding site, but 12 contain at least one P300 binding site, 4 contain at least one CBP binding site and 3 contain at least one of both a P300 binding site and a CBP binding site.

TABLE 1

Analysis of transcription factor binding site of APC-associated genes

| | |
|---|---|
| NCBI gene accession number of APC-associated genes containing P300 binding site | L13740, M29039, U15932, J02931, X75918, M92843, M22489, X63741, AL031432, L05072, D78579, J04076, AB014569, X94216, AL023584, D86181, U04636, AF039843, U08015, U43142, U79259, AF068197, J04111, AF050110, S81439, U07802, AL096858, AF022375, U81607, D50917, Z25821, U59863, U35735, U87460, U27655, |

TABLE 1-continued

Analysis of transcription factor binding site of APC-associated genes

| | |
|---|---|
| NCBI gene accession number of APC-associated genes containing CBP binding site | U58334, AC004475, Z25821, U85267, D38537 M92843, AL034132, L05072, D78579, AL023584, D86181, U79259, J04111, S81439, AL096858, M22299, U53831, L38696, AB028069 |
| NCBI gene accession number of APC-associated genes containing P300 and CBP binding site | M92843, AL034132, L05072, D78579, AL023584, D86181, U79259, J04111, S81439, AL096858 |
| NCBI gene accession number of APC-highly associated genes (average induction > 2) containing P300 binding site | L13740, M29039, J02931, X75918, M92843, X63741, AL031432, L05072, AB014569, X94216, U04636, U87460 |
| NCBI gene accession number of APC-highly associated genes (average induction > 2) containing CBP binding site | M92843, AL0314323, L05072, M22299 |
| NCBI gene accession number of APC-highly associated genes (average induction > 2) containing both P300 and CBP binding site | M92843, AL0314323, L05072 |

P300/CBP is capable of binding to β-catenin to activate TCF (V. S. Ossovskaya and N. W. Bunnett, *Physiol Rev.*, 2004, 84: 579-621). Therefore, the underlying mechanism of improving cell viability by APC may reside in that DNA fragment of expressed APC-regulated gene could reduce availability of β-catenin in cell nucleus by its binding to P300/CBP, β-catenin, and TCF, resulting in decrease of cell mobility and division so as to increase cell viability of LPS-stimulated endothelial cells.

Gene therapy is provided in the present invention to treat sepsis induced by bacterial infection. The gene therapy is through competitive or decoy DNA sequence to exert activity of APC associated transcription factor to increase cell viability of LPS-stimulated cells. The technology is called transcription factor decoy strategy. The carrier in the present invention is used to introduce TCF oligonucleotide decoy into cell, wherein the preferred nucleotide is deoxyribonucleic acid (DNA). TCF DNA decoy can directly reduce TCF availability.

The present invention is further illustrated by the following examples; it should be understood that the examples and embodiments described herein are for illustrative purposes only and should not be construed as limiting the embodiments set forth herein.

EXAMPLES

General Experimental Reagents, Instrument and Apparatus

1. Experimental Instruments

1. $CO_2$ incubator: NuAire, Inc. (MN, USA). NU-4950; 2. liquid nitrogen tank: Air Liquid (Gutenberg, France), ARPEGE40; 3. laminar flow: (Cheng Sang, Taipei, Taiwan); 4. Pipette add: Drummond Scientific Company (Broomall, Pa., USA), Serial NO: 14-4000100; 5. Vacuum pump: Tokyo Rikakikai Co., Ltd. (Tokyo, Japan), Serial NO: A-3S; 6. Electronic Balance: Sartorius (Goettingen, Germany), GM1502; 7. microbalance: Sartorius (Goettingen, Germany), BP211D; 8. pH meter: Metter Toledo (Goettingen, Germany), MP220; 9. hot plate: Thermolyne (Dubuque, Id., USA), SP18425; 10. Votex mixer: Thermolyne (Dubuque, Id., USA), M37645; 11. autoclave: HUXLEY (Taipei, Taiwan), HL-321; 12. Continuous-wave Disk Mapping Spectrometer: Bio-tek Instruments, Inc. (Winoosli, Vt., USA), MQX200; 13. UV/Visible Spectrophotometer: Varian (Victoria, Australia), Model: Cary-50, Serial number: EL0311-7483; 14. ultra-high speed centrifuge: Model #CP80MX, roter: #P40ST-1591, Hitachi Koki (Tokyo, Japan); 15. high-speed refrigerated centrifuge: Sorvall Instruments (Foster, Conn., USA), RC-5C centrifuge: Heymle Co. (Franklin, Wis., USA) Z233 MK-2; 16. desktop micro-centrifuge: Eppendorf (Hamburg, Germany), 5415D; 17. Desktop centrifuge: Hettich Zettich (Barsbüttel, Germany), D-78532; 18. Vacuum decompression concentrator: Panchum Scientific Corp (Taipei, Taiwan), CES-8000; 19. oil-free vacuum pump. Panchum Scientific Corp (Taipei, Taiwan), VP90; 20. gel casting cassette: Hoefer Co (Rothpfaffenhofen, Germany), NO-SE2000; 21. electrophoretic transfer cell: Bio-Rad. (Fercules, Calif., USA), 170-3930; 22. power supply: Bio-Rad., Power PAC 300; 23. oscillator: Stovall Co. (Greenboro, N.C., USA); 24. semi-dry electrophoretic transfer: Idea Scientific Company, P.O. (Las Vegas, Nev., USA) BOX 13210, MINNEAPOLIS MN55414; 25. radiographic film cassette: Amersham Biosciences Co. (Picataway, N.J., USA), Hyercassette; 26. 4° C. refrigerator: HIPOINT (Taipei, Taiwan), MS-302; 27. −20° C. freezer: Frigidire (Augusta, Ga., USA), FFU21C3AW; 28. −80° C. freezer: SANYO (Osaka, Japan), MDF-192; 29. water bath: Hitachi (Tainan, Taiwan); 30. flow cytometer: Becton Dickinson and Company (Franklin Lakes, N.J., USA), NO-FACS calibur; 31. fluorescence microscope: Nikon Optical Co., Ltd. (Tokyo, Japan), TE2000-U; 32. Image-Pro Plus: Media Cybernetics, Inc. (Silver spring, MD, USA), V 6.1; 33. inverted optical microscope: Nikon Optical Co., Ltd. (Tokyo, Japan), TS-100; 34. confocal microscope: Zeiss (Oberkochen, Germany), LSM510; 35. in NO sensor: Innovative Instruments, Inc. (Wake Forest, N.C., USA), 3768-F; 36. amiNO sensor: Innovative Instruments, Inc., 700-J; 37. infrared spectroscopy: Perkin Elmer (Boston, Mass., USA), 33856.

2. Experimental Apparatus 1. cell culture plate (35×10 mm tissue cultured dishes): BD Falcon (Ontario, Canada), DF353001; 2. cell culture plate (60×15 mm tissue cultured dishes): Corning Incorporated (New York, N.Y., USA), 430166; 3. micropipette (2.0-20, 20-20, and 100-1000 μL): Eppendorf, CEP-3111000033, CEP-3111000050, CEP-3111000068; 4. 1 mL pipette: Greiner bio-one, Cellstar (Kremsmunste, Austria), 604181; 5. 5/10 mL pipette: Corning Incorporated, Costar, 4487, 4488; 6. centrifuge tube (15/50 mL): BD Falcon, DF352095, DF352070; 7. high-speed centrifuge tube: Hitachi, Centrifuge Ware, 33290-1A; 8. cryogenic vial: Nunc. Co. (Frankfurt, Germany), Cryo Tube™, 363401; 9. filter: Corning Incorporated, Corning, 431161; 10. blood collection tube: BD Vacutainer 10 ml, 8000999; 11. locking dialysis membrane clamp: Spectrum™ (Geneva, Switzerland), 13275, with a width of 3 mm; 12. dialysis membrane: Spectrum™, pore size MW. 10,000, with a width of 8 mm; 13. glass syringe: Hamilton Co. PN: E084-XPJ-995041; 14. haemocytometer: Nunc. Co., No: 269620; 15. 96F Microwell Plate-SH: Nunc. Co., No: 269620.

3. Experimental Reagents 3.1 Cell Culture 1. human aortic endothelial cell: Cascade Biologics; 2. M199 Medium: Sigma (SanLouis, Mo., USA), M-5017; 3. Cosmic Calf Serum: Perbio, Hyclone, NO: SH30413.03; 4. low serum growth supplement (LSGS): Cascade Biologics, S-003-10; 5. sodium pyruvate (SP): Sigma, 58636; 6. L-glutamine: Sigma, G-7513; 7. gentamicin solution: Sigma, G-1272; 8. antibiotic antimycotic solution: amphotericin B/penicillin/streptomycin, (APS) Sigma, A-5955; 9. sodium bicarbonate: J. T. Baker (Phillipsburg, N.J., USA), 3506-01; 10. Dulbecco's phosphate buffered saline (DPBS): Sigma, D-5625; 11. gelatin: Sigma, G-1890; 12. dimethyl sulfoxide (DMSO): Sigma, D-8779; 13. 10× Trypsin-EDTA: Sigma, T-4174; 14. Liquid nitrogen: Boc Lienhwa Ind. Gases (Taiwan).

3.2 Cellular Experiment 1. lipopolysaccharide from *E. coli* 0111B4: Sigma, L-263; 2. recombinant Activated protein C: Eli Lilly, XP6590TTWX; 3. DNA synthesis: Bio basic Inc. (Ontario, Canada).

3.3 Preparation of Low Density Lipoprotein (LDL)

1. sodium chloride: Riedel-deHaen, 31434; 2. potassium bromide: Sigma, P-9881; 3. sucrose: Sigma, S-5016; 4. argon gas: Dry Ice Technology Co., Ltd.

3.4 Preparation of Lysis Buffer

1. Tris: USB, 75825; 2. Triton X-100: Sigma, T-8787; 3. phenylmethylsulfonyl fluoride (PMSF): Sigma, P-7626; 4. protease inhibitor cocktail tablets: Roche diagnostics (New York, USA), 11 836 170 001.

3.5 Determination of Protein Concentration

1. BCA™ Protein Assay Reagent Kit: Pierce, 23227; 2. Albumin Standard: Pierce, 23209; 3. Acetone: J. T. Baker, 9508-03.

3.6 Preparation of Carrier 1. poly-L-lysine: Sigma, P-3995; 2. palmitoyl chloride: Aldrich, P78; 3. triethylamine: Sigma, T0886.

3.7 Measurement of Nitric Oxide 1. sodium nitrite: Sigma, 53421; 2. potassium iodide: Wako Pure Chemical Industries, LTD (Osaks, Japan); 3. sulfuric acid: J. T. Baker, 9684-05.

3.8 Western Blotting 1. 40% acrylamide/bis, 29:1, solution: J. T. Baker, 4969-00; 2. Tris: USB, 75825; 3. glycine: J. T. Baker, 4059-02; 4. Tween 20: Sigma, P-5927; 5. HCl: J. T. Baker, 953501; 6. sodium dodecyl sulfate (SDS): J. T. Baker, 409504; 7. ammonium persulphate (APS): Sigma, A-9164; 8. N,N,N',N'-Tetramethylethylenediamine (TEMED): Sigma, T-7024; 9. glycerol: Sigma, G-5516; 10. methanol: J. T. Baker, 9054-01; 11. butanol: Mallinckrodt, 3041; 12. acetic acid: J. T. Baker, 9508-03; 13. Anti-β-actin: Chemicon, MAB1501; 14. Anti-β-catenin: Sigma, C-2206; 15. rat anti-mouse IgG1: BD, 50331; 16. enhanced luminol reagent and oxidizing reagent: Perklin Elmer, NEL-105; 17. PVDF membrane: Perklin Elmer, 881716-1200; 18. developer and replenisher: Kodar, KP 85056-C; 19. fixer and replenisher: Kodar, KP 85054-C; 20. film: Kodar, 263 020 08; 21. skimmed milk: Anchor® skimmed milk powder.

3.9 Measurement of Cell Viability 1. trypan blue solution (0.4%): Sigma, T-8154.

General Experimental Methods

1. Culture of Human Aortic Endothelial Cells 1.1 Preparation of Reagents

M199 stock: 9.62 g powder of M199 Medium and 2.2 g sodium bicarbonate were mixed with 1 liter of ddH$_2$O and then adjusted to pH7.4, filtered through 0.22 µm Millipore Filter to sterilize and stored at 4° C.

M199 culture medium: M199 stock was supplemented with 10% Cosmic Calf Serum, 10% sodium pyruvate and 10% L-glutamine, 10% low serum growth supplement (LSGS), 10% antibiotic antimycotic solution (APS) and 5% gentamicin solution and then stored at 4° C.

DPBS: 9.6 g DPBS powder was dissolved in 1 L ddH$_2$O, adjusted to pH7.4, filtered through 0.22-µm Millipore filter to sterilize and stored at 4° C.

Cryoprotectant: To 90% M199 culture medium was added 10% sterile dimethyl sulfoxide (sterile DMSO).

Gelatin solution: 1.5 g gelatin was dissolved in 100 mL DPBS by boiling, followed by being immediately filtered through 0.22-µm Millipore filter to sterilize and stored at 4° C.

1× Trypsin-EDTA solution: To 1 mL 10× Trypsin-EDTA stock was added 9 mL DPBS to obtain 1× Trypsin-EDTA solution.

1.2 Subculture

Human aortic endothelial cells (HAEC) was used in cell subculture in the following examples.

1.2.1 Preparation of Gelatin-Coated Plate

To increase cell attachment, 1.2 mL gelatin solution was added to a cell culture plate (60×15 mm tissue cultured dish) and placed in incubator at 37° C. for 15 mins. The plate was washed with 3 mL DPBS by agitating and removing DPBS to remove remaining gelatin.

1.2.2 Cell Thawing

Cryogenic vial containing cells was removed from liquid nitrogen and their caps loosened to release pressure difference and then placed in 37° C. water bath to allow cells to thaw and form a cell suspension. The cell suspension in the cryogenic vial was transferred to centrifuge tube and centrifuged at 10×g for 7 mins. Supernatant was removed. A cell pellet at bottom of the centrifuge tube was resuspended with 1 mL culture medium and placed on a gelatin-coated plate. 2 mL culture medium was added to the gelatin-coated plate and evenly distributed by agitation. The gelatin-coated plate containing cells was then placed in a CO$_2$ incubator, at 37° C. Culture medium was replaced every two days. Cells were examined through observing their morphology.

1.2.3 Cell Subculture

The cells were thawed and grown in a cell culture plate for 4 days. The confluent cells were divided into three new gelatin-coated plates as follows. The plate was removed from the incubator. Culture medium was removed by suction and cells were washed with 3 mL DPBS to remove excess trypsin inhibitor. 0.6 mL 1× trypsin-EDTA solution was evenly distributed over the cells and then removed after 10 seconds. The plate was flipped and cells were observed by microscope to confirm detachment from the plate. Once detached, cells were resuspended into 9 mL fresh culture medium, divided into and evenly distributed on 3 new gelatin-coated plates, each for 3 mL. The divided cells were cultured in the CO$_2$ incubator held at 37° C. for 4 days to be confluent and then subjected to subsequent experiments 3 days later.

1.2.4 Cell Preservation

Cells might be selectively frozen for later use. Culture medium in the plate containing confluent cells was removed by suction. 3 mL of DPBS was added in and removed from the plate by washing 0.6 mL 1× trypsin-EDTA solution was added to the plate for 10 seconds to detach cells from the plate. 2 mL of culture medium with 10% cryoprotectant was added to each plate and pipetted to detach cells. The cells were collected and divided into 2 cryogenic vials. The vials were held at −80° C. for a day and then stored in liquid nitrogen.

2. Purification of Low Density Lipoprotein (LDL)

Low density lipoprotein was prepared by density gradient centrifugation as following.

2.1 Preparation of Reagents

Stock salt solution: 153 g sodium chloride and 354 g potassium bromide was dissolved in one liter pure water as the stock salt solution with a density of 1.289 $g/cm^3$.

Sodium chloride solution: a solution containing 0.15 M sodium chloride with a density of 1.006 $g/cm^3$ was prepared as sodium chloride solution.

Sucrose solution: a solution containing 50% w/w sucrose, 150 mM NaCl, 0.24 mM EDTA, pH7.4 was prepared as sucrose solution.

Whole blood: Blood was obtained from healthy donors in Dalin Branch of Buddhist Tzu-Chi General Hospital (Chiayi, Taiwan), following standard protocols.

Gradient solution for density gradient centrifugation: a solution was prepared by mixing stock salt solution and sodium chloride solution according to the following formula:

$$A \times 1.289 + B \times 1.006 = (A+B) \times X$$

wherein A represents volume of stock salt solution; B represents volume of sodium chloride solution; and X represents a desired density.

2.2 Determination of Density of Solution

Equal volumes of water and analyte were measured. The density of the analyte was determined by ratio of the analyte to the water by weight.

2.3 Process for Isolating LDL

Serum was obtained by centrifuging the whole blood, and then its density was examined and adjusted to 1.090 g/mL with potassium bromide solution, if necessary. Solutions with predetermined densities were placed in a centrifuge tube as indicated in Table 2 to form a density gradient as follows. 1 mL of solution with a density of 1.182 g/mL, 5 mL of serum, 1 mL of solution with a density of 1.063 g/mL, 2 mL of solution with a density of 1.034 g/mL, 1 mL of solution with a density of 1.019 g/mL were sequentially added into the centrifuge tube. The tubes were carefully balanced by adding solution with a density of 1.006 g/mL if required before being centrifuged by ultra-high speed centrifuge (Model #CP80MX, rotor: #P40ST-1591) at 29,500 rpm at 12° C. for 24 hours.

TABLE 2

Distribution of density gradient for ultra-high speed centrifugation

| Density (g/mL) | Volume (mL) |
| --- | --- |
| 1.007 | 1 |
| 1.019 | 1 |
| 1.034 | 2 |
| 1.063 | 1 |
| 1.090 (serum) | 5 |
| 1.182 | 1 |

After centrifuge, obvious liquid layers in the centrifuge tube could be observed. The bottom of the centrifuge tube was pierced separate the liquid layers. After discarding a bottom layer, fractions of 3 to 4 drops were collected in microtubes. The collected fractions were stored in the dark to avoid oxidation of LDL to form oxidized LDL (oxLDL). Fractions with density ranging from 1.019 to 1.063 g/mL, containing isolated LDL, were identified.

2.4 LDL Preservation

Isolated LDL to which one-fourth of equal volume of sucrose solution was added were filled with argon gas and then stored at −80° C.

2.5 Use of LDL

The stored isolated LDL was thawed and dialyzed in PBS at 4° C. for 24 hours to be ready for use.

3. Determination of Protein Concentration by Colorimetry

BCA™ Protein Assay Kit was used for determining cell protein concentration in the following examples and albumin was used as standard.

3.1 Preparation of Reagents

Working solution: BCA™ Protein Assay Reagent A and Reagent B were mixed at a ratio of 50:1.

Standard solution: Three different concentrations of standard solution, 2,000 μg/mL, 1,000 μg/mL and 500 μg/mL, were prepared from Standard of BCA™ Protein Assay Kit (2,000 mg/mL). The working solution was used as a blank.

Acetone: acetone was cooled at −20° C. before use.

3.2 Determining LDL Concentration

50 μL of samples including 0, 500, 1,000, 2,000 μg/mL standard solutions and the LDL anlyate were respectively added into 200 μL pre-cooled acetone and extracted from oil by agitation, followed by centrifugation at 16,000×g for 10 mins. Supernatant was aspired. Process as described above was repeated three times. Protein pellets of samples formed in a final step of the process were dried by vacuuming to completely evaporate remaining acetone. The dried protein pellet of each sample was dissolved by adding 1 mL of working solution and incubating in 37° C. water bath for about one hour, and sonicating if required. 200 μL of the treated samples was transferred into 96-well plate. Absorbance at 562 nm wavelength of each treated sample was measured by spectrometer.

3.3 Measurement of General Protein Concentration

10 μL of samples of 0, 500, 1,000, 2,000 μg/mL standard solutions and general protein analytes were transferred into a 96-well plate respectively and diluted with 200 μL working solution and then placed in 37° C. incubator for 30 mins. The diluted samples in the plate were removed from the incubator and degassed. Absorbance at 562 nm wavelength of each diluted sample in the plate was measured by spectrometer. A calibration curve was made in accordance with the four known concentrations of the standard solutions for calculating concentration of the analytes.

4. Preparation of Composition Containing DNA Decoy

Poly-L-lysine was used as carrier in the following examples, by nature of its positive charge to bind to DNA, and was modified by conjugating to a hydrophobic group that contains 16 carbons to protect and facilitate its recipient (S. W. Kim, J Control Release. 1998, 53:175-182) to enter cells.

4.1 Synthesis of Carrier 30 mg poly-L-lysine was dissolved in 2 mL DMSO. 20 mg palmitoyl chloride was added into the dissolved poly-L-Lysine in DMSO, which reacts with the amino group in Lysine, to form a mixture. 10 μL triethylamine was added into the mixture with stirring for 2 hours. When reaction completed, acetone was slowly added into the mixture to force crystallization of product. The mixture was then centrifuged at 13,400×g for 10 mins to obtain pellet. Pellet was dissolved in methanol. Acetone was then added into the dissolved pellet in methanol to force crystallization of product, followed by centrifugation to obtain palmitoyl poly-L-Lysine (pal-P-Lys).

4.2 Preparation of Composition

Pal-P-L-Lys and LDL were mixed at a ratio of 1:1 at 37° C. for 1 hour and then mixed with DNA at about a ratio of 1:1 to a final ratio of pal-P-L-Lys:LDL:DNA of 1:1:1 by weight.

5. Measurement of Nitric Oxide

In the following examples, in NO and amiNO sensors were used. The underlying principle is that NO in an analyte diffuses through membrane mounted in front of the amiNO sensor and is oxidized by electrode, resulting in change of potential to modulate current, and then the modulated current was recorded by in NO sensor. Concentration of NO in the analyte was calculated in accordance with comparison to standards.

Measurement of Standards was performed by adding 1 mole $NO_2^-$ and iodide ion ($I^-$) to produce 1 mole NO, as following formula:

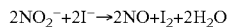

$$2NO_2^- + 2I^- \rightarrow 2NO + I_2 + 2H_2O$$

A calibration curve was made in accordance with concentrations and measured currents of standards.

5.1 Preparation of Reagents

Calibration solution: To 2 mL 1 M $H_2SO_4$ was added 18 mL dd$H_2O$ and 20 mg potassium iodide.

Nitrite standard: 6.9 mg $NaNO_2$ was added into 10 mL dd$H_2O$ and prepared as 10 mM stock solution for further dilution.

5.2 Preservation and Maintenance of NO Sensors

The in NO was turned off and amiNO sensor was preserved in dd$H_2O$. For maintenance, 1% low-foam enzyme cleaner was used to wash the sensors for 1-2 hours for clearance of residues in the sensors.

5.3 NO Measurement

The amiNO sensor preserved in water was inserted into in NO for at least 3 hours to warm-up and then was placed in 1 mL calibration solution. When a currant value was stably provided, bottom "Zero" was pressed for normalization. Nitrite standards were injected to form a final concentration of 12.5 nM, 25 nM, 50 nM and 75 nM. Values of current value divided by concentration were calculated and entered, followed by entering "Exam" to complete calibration, and thus sensors were ready for measuring samples.

6. Determination of Cell Viability

General method for determining cell viability includes MTT assay and trypan blue staining. In the following examples, trypan blue staining was used for determining cell viability.

6.1 Preparation of Reagents

Trypsin-EDTA: 1× Trypsin-EDTA was obtained from mixing 10% total amount of trypsin-EDTA (10×) and 90% total amount of DPBS.

DPBS: 9.6 g DPBS powder was dissolved in 1 L dd$H_2O$, adjusted to pH7.4, filtered to be sterile and stored at 4° C.

6.2 Process

Cells were washed with DPBS. Trypsin-EDTA solution was added to cells in 35 mm plate and then the plate was scraped, flushed with 0.5 mL DPBS and transferred to a 1.5 mL-microtube, mixed with 0.5 mL trypan blue and then incubated at 37° C. for 7 mins. The cells were obtained by centrifuging at 400×g for 7 mins. Supernatant was decanted and the cells were washed by adding 1 mL DPBS and centrifuging at 400×g for 7 mins to remove remaining trypan blue. Cells were then suspended in 0.5 mL DPBS to form a cell suspension. A counting chamber of a haemocytometer was cleaned with water, wiped with lens cleaning paper and sprayed with 70% ethanol on surfaces of a cover glass and the counting chamber before air drying. The cover glass was placed to cover both counting chambers. To each counting chamber 10 μL of cell suspension was added. The numbers of dead cells and viable cells were recorded and analyzed.

7. Purification of Cellular Organelles

Dounce homogenizer with loose type A pestle and loose type B pestle was used, wherein a gap between pestles ranges from 0.0035" to 0.0055" for loose type, and 0.0010" to 0.0030" for tight type. Loose type A pestle was used in the following examples.

7.1 Preparation of Reagents

DPBS: 9.6 g DPBS powder was dissolved in 1 L dd$H_2O$, adjusted to pH7.4 at 25° C., filtered to be sterile and stored at 4° C.

Lysis buffer: 36.3 mg Tris was dissolved in 12.86 mL dd$H_2O$ and adjusted to pH7.4 and a volume of 15 mL. On the day of experiment, 1 mg PMSF was weighed and dissolved in 200 μL isopropanol as PMSF solution. 52.5 μL PMSF solution was added into Tris-SDS solution and used to prepare a Lysis buffer containing 20 mM Tris-HCl, 1× protease inhibitor and 0.1 mM PMSF, and then stored at 4° C. for use.

8. Western Blotting

To analyze a specific protein, proteins with different molecular weight could be separated by SDS-PAGE and transferred to a PVDF membrane. The PVDF membrane was sequentially subject to incubation with primary antibody and secondary antibody and substrate which reacts with enzyme on the secondary antibody and could emit a detectable signal for detecting the specific protein and determining its molecular weight and amount.

8.1 Preparation of Reagents 1.5 M Tris-Base: To 36.342 g Tris-base was added dd$H_2O$ to a final volume of 180 mL, adjusted pH8.8 and a volume of 200 mL, and then stored at 4° C.

1.0 M Tris-base: To 24.228 g Tris-base was added dd$H_2O$ to a final volume of 180 mL, followed by being adjusted pH value to 6.8 and volume to 200 mL, and then stored at 4° C.

10% SDS solution: 20 g SDS was dissolved in 100 mL dd$H_2O$ and adjusted to a final volume of 200 mL.

10% ammonium persulfate (APS) solution: 0.05 g APS was dissolved in 0.5 mL dd$H_2O$, which was freshly prepared before use.

5×SDS gel-loading buffer (5× sample buffer): 250 mM Tris-base was diluted from 2.5 mL 1.0 M Tris-base (pH6.8). 1 g SDS was dissolved in the 250 mM Tris-base to a final concentration of 10% SDS, followed by addition of 0.05 g bromophenol blue, 5 mL glycerol (about 6.15 g) and dd$H_2O$ to a final volume of 10 mL. Obtained 5×SDS gel-loading buffer was stored at room temperature and shaken before use.

5× Tris-glycine buffer (running buffer): 15.1 g Tris-base and 94 g glycine were added into 10 mL 10% SDS solution and adjusted to 1000 mL and pH 8.3.

1× Tris-glycine buffer (running buffer): 200 mL 5× Tris-glycine buffer was diluted to 1000 mL with water.

7.5% lower gel solution: 5.425 mL ddH$_2$O, 1.875 mL 40% acrylamide, 2.5 mL 1.5 mM Tris (pH 8.8), 0.1 mL 10% SDS solution, 0.1 mL 10% APS and 0.006 mL TEMED were mixed and prepared as a 10 mL lower gel solution.

5% upper gel solution: 2.867 mL ddH$_2$O, 0.503 mL 40% acrylamide, 0.5 mL 1.5 mM Tris (pH 6.8), 0.04 mL 10% SDS solution, 0.04 mL 10% APS and 0.004 mL TEMED were mixed and prepared as a 4 mL upper gel solution.

Transfer buffer: 3.03 g Tris, 14.4 g glycine and 1 L ddH$_2$O were mixed as Tris-glycine solution and then stored at 4° C. 100 mL methanol was added to 400 mL Tris-glycine solution as 500 mL transfer buffer, and stored at 4° C.

PBST: 81.82 g NaCl, 1.02 g NaH$_2$PO$_4$.H$_2$O, 13.15 g Na$_2$HPO$_4$ were added into 900 mL ddH$_2$O with stirring, followed by being adjusted to pH 7.4 and 1,000 mL with ddH$_2$O, as 10×PBS. 100 mL 10×PBS was added to and mixed with 900 mL ddH$_2$O and 0.55 g Tween 20 as PBST.

PBST+skim milk: 1.5 g skim milk was added into 30 mL PBST with stirring.

Anti-β-actin (primary antibody): 2 μL anti-β-actin was added into 30 mL PBST as 1:15,000 dilution by volume.

Anti-β-catenin (primary antibody): 7.5 μL Anti-β-catenin was added into 30 mL PBST as 1:4,000 dilution by volume.

Rat-anti-mouse antibody (secondary antibody): 3 μL rat-anti-mouse antibody was added into 30 mL PBST as 1:10,000 dilution by volume, and further supplemented with 1.5 g skimmed milk with stirring.

ECL: 2 mL ECL Coloring Reagent A and 2 mL Coloring Reagent B were mixed in volumetrically equal proportions.

Fixer: 100 mL fixer stock solution was mixed into 360 mL ddH$_2$O.

Developer: 100 mL developer stock solution was mixed into 360 mL ddH$_2$O.

8.2 Experimental Process 8.2.1 Gel Preparation

Gel casting cassette was assembled, followed by injecting lower gel solution to align the top of the injected lower gel solution at 80% total height and to avoid formation of bubble in the injected lower gel solution. N-butanol was gentle layered on the top of the injected lower gel solution. Bubbles formed during injection were removed. The lower gel solution was stood for 30 mins for casing. N-butanol was pooled out and cleaned up. Upper gel solution was then added. Comb was inserted into the upper gel solution and stood for 30 mins for gel consolidation to form sample wells. After consolidation of the upper gel solution, the comb was removed and sample wells were formed.

8.2.2 SDS-PAGE Analysis

Samples was evaluated by protein concentration and an amount of each sample containing 25 μg protein was injected into a sample well. The prepared gel was removed from the gel casting cassette and then placed into electrophoresis tank containing electrophoresis buffer. One-fourth of total volume of 5× sample buffer was mixed into each sample and incubated in 95° C. water bath for 5 mins to denature proteins and break the disulfide bonds and then transferred on ice for 2 mins for immediate cooling to prevent DDT-reacted protein to form disulfide bonds again. The treated samples were slowly loaded into sample wells, each well for 15 μL of one sample. During loading of samples, flooding of sample in adjacent wells was avoided. When loading of samples was finished and ready for electrophoresis, electrodes were connected and the electrophoresis was started and run at a voltage of 100 volts for 2 hours.

8.2.3 Transferring to PVDF Membrane

After filter papers and PVDF membrane were tailored, PVDF membrane was immersed in methanol for 30 seconds and then rinsed with transfer buffer for activation. The lower gel was gently moved out. The filter papers, PVDF membrane, gel, filter papers were in sequence placed in semi-dry electrophoretic transfer from anode to cathode and then transferred at a voltage of 12 mV for 1 hour and thus proteins were transferred onto PVDF membrane.

8.2.4 Blocking

The transferred PVDF membrane was immersed in 30 mL PBST buffer with 5% skim milk and subject to agitation at room temperature for 1 hour and stored at 4° C. overnight.

8.2.5 Hybridization

PVDF membrane was washed with PBST four times for 5 mins. Primary antibody and PVDF membrane were placed centrally in a tray and agitated for 1.5 hours, followed by washing with PBST four times, each time for 5 mins. Secondary antibody was added onto the membrane and agitated for 1 hour and then washed with PBST four times, each time for 5 mins.

8.2.6 Development and Exposure

PVDF membrane was immersed in a mixture of ECL coloring reagents A and B mixed at a ratio of 1:1. The membrane was then placed in a transparent PE bag, held in radiographic film cassette and topped with an X-ray film for exposure. The film was sequentially placed into developer, water and fixer for film development.

Reference Example

APC Reduces Protein Content of Cytoplasmic β-Catenin

Woo et al. disclosed that lipopolysaccharide (LPS) at 100 μg/mL is sufficient to change amount of intracellular cytokine (C. H. Woo, et al., *Mol. Cells.*, 2002, 13: 470-475). Li et al. treated human endothelial cells stimulated with LPS (Y. Li, et al., *Zhejiang. Univ Sci. B.*, 2006, 7: 899-905). Accordingly, in the present example, dose of LPS was 100 ng/mL and dose of APC was 70 ng/mL.

In the present reference example, amount of cytoplasmic β-catenin in human aortic endothelial cells stimulated with LPS was evaluated. Amount of cytoplasmic β-catenin in human aortic endothelial cells stimulated with LPS for 6 hours in the presence of APC or not for 30 mins was determined by western blotting, as follows:

Endothelial cells were treated with 1 mL of 100 ng/mL LPS in a 35 mm plate for 6 hours was treated with 70 ng/mL APC for 30 mins. Amount of cytoplasmic β-catenin was evaluated by electrophoresis and western blotting (n=2), each well for 25 μg protein, wherein endothelial cells without being treated with LPS were used as control.

As shown in FIG. 1, β-catenin was found to dramatically drop at 30 mins after APC administration.

For analysis of the effect of APC on cell viability of endothelial cells, endothelial cells were subject to treatment of 100 ng/mL LPS for 6 hours and subsequent treatment of 17 ng/mL APC for 12 hours. Cell viability was determined (n=3~9).

Figure 2:
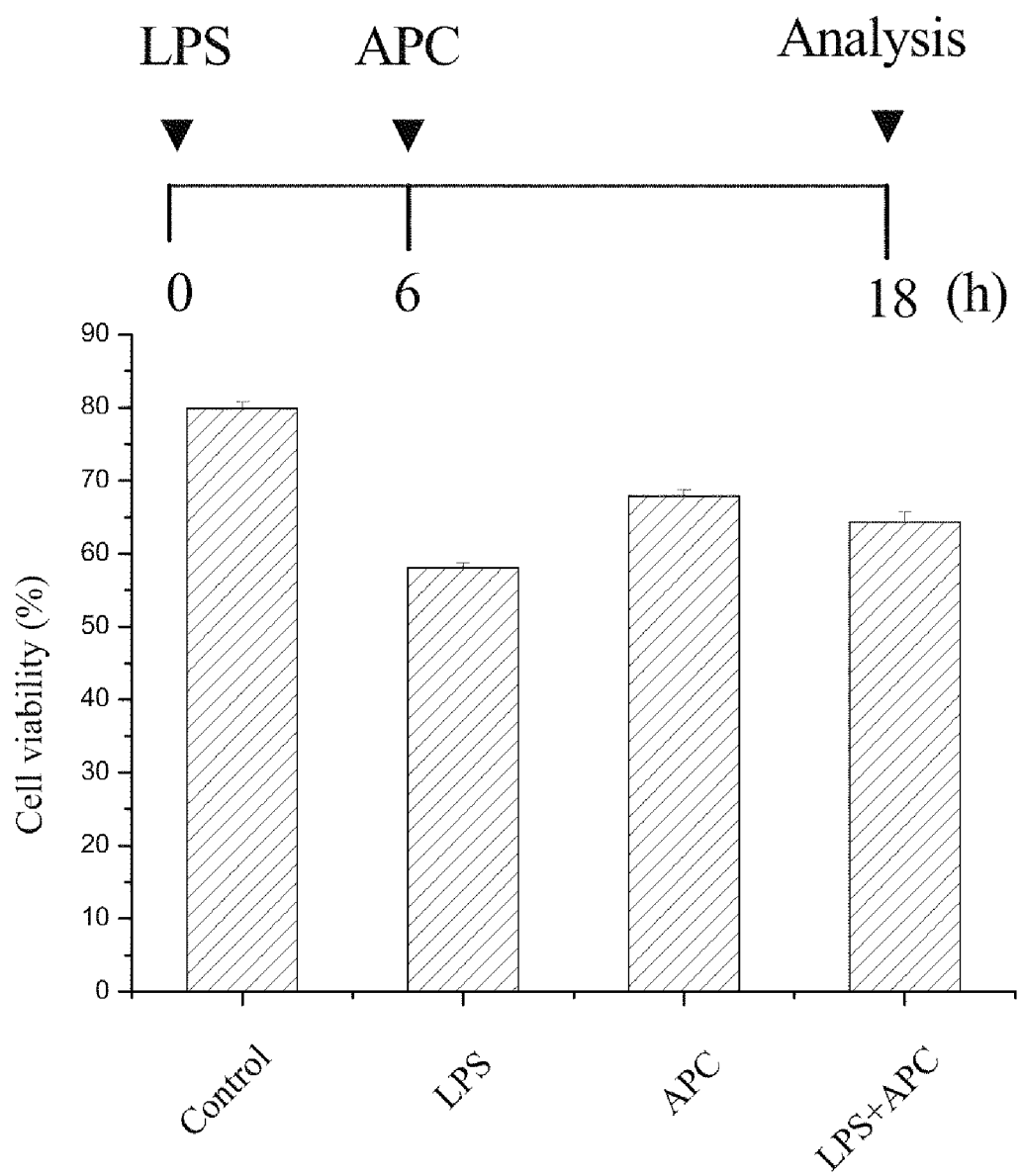
FIG. 2 illustrates effect of APC treatment on cell viability of endothelial cells stimulated with LPS.

As shown in FIG. 2, cell viability after 18 hours LPS treatment dropped from 80% to 58%. Cell viability of the group of 6-hour LPS treatment and 12-hour APC treatment was 64%, increasing 6%. The results confirmed that APC indeed could increase cell viability of cells stimulated with LPS.

Preparation Example

Carrier Preparation

Figure 3:
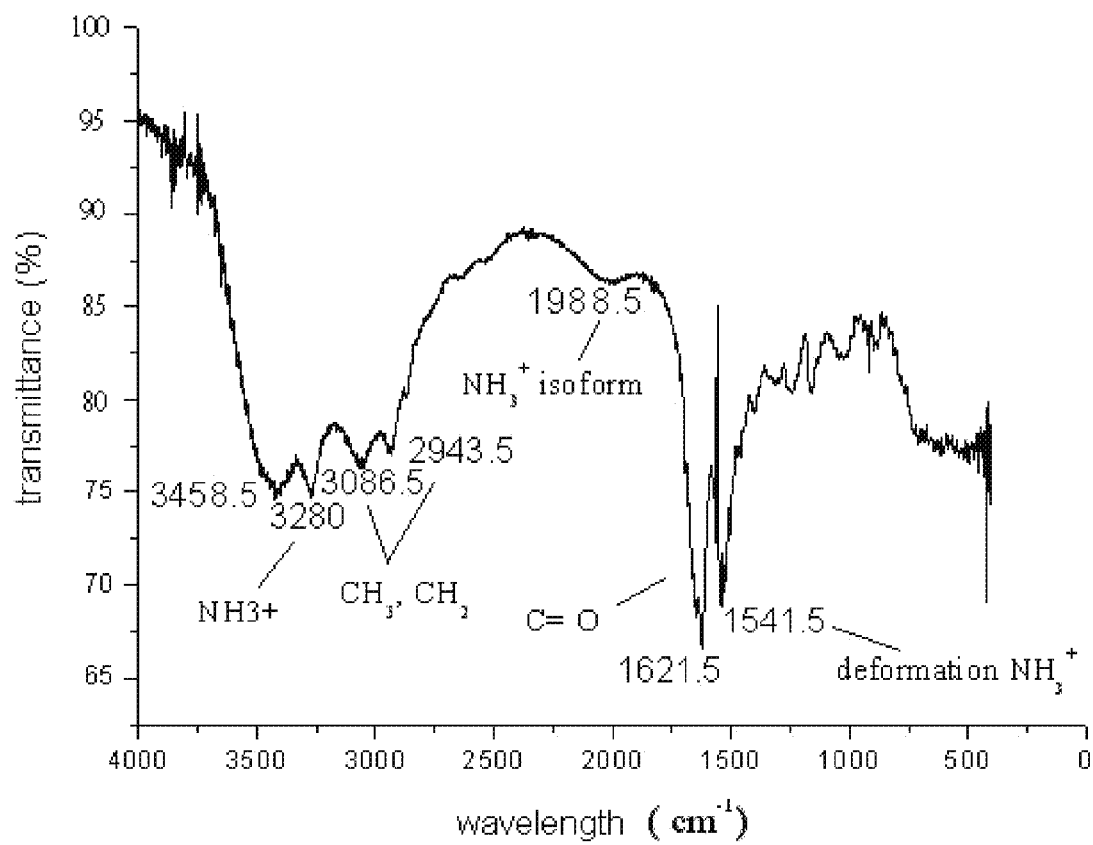
FIG. 3 illustrates FTIR spectrum of P-L-Lys, averaged and corrected against a KBr spectrum.
Figure 4:
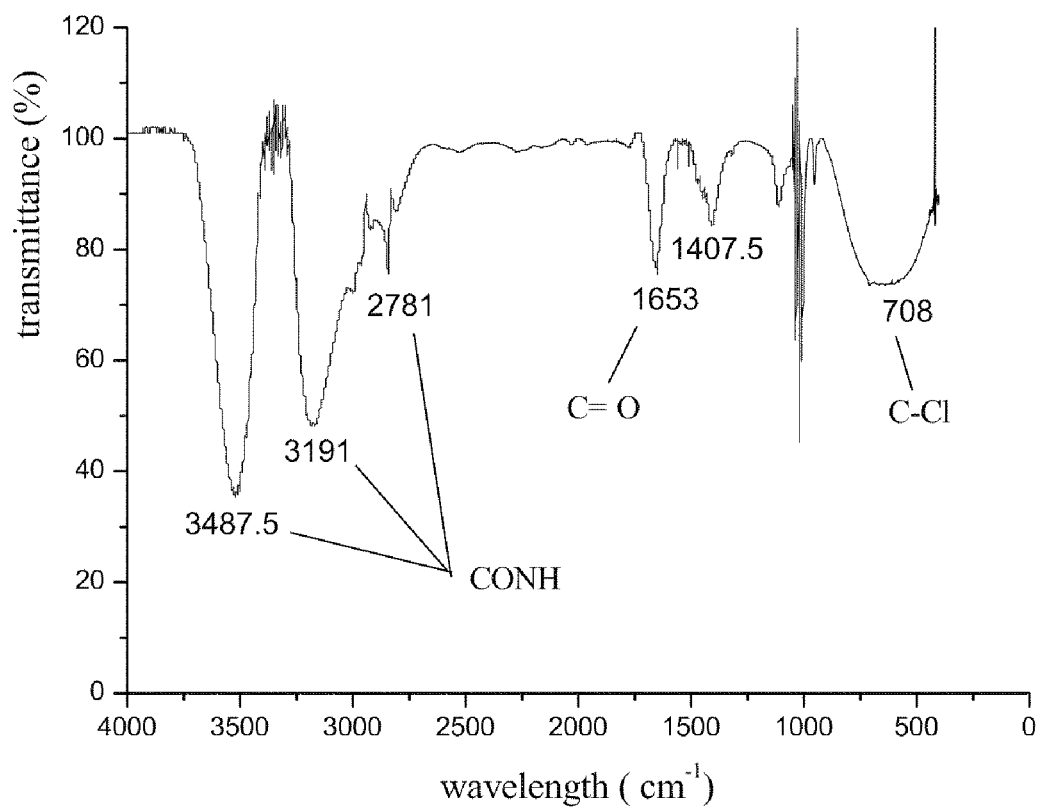
FIG. 4 illustrates FTIR spectrum of pal-P-L-Lys, averaged and corrected against a methanol spectrum.

In the present example, DNA was introduced into cells with pal-P-L-Lys-LDL-DNA system in accordance with method as described in "4.1 Synthesis of carrier" in "General materials and methods". The yield of pal-P-L-Lys from P-L-Lys and palmitoyl chloride was 40%, which was analyzed by FTIR. FIGS. 3 and 4 are spectrum of P-L-Lys, wherein 3280 cm$^{-1}$ represents $NH_3^+$, 3086.5 cm$^{-1}$ and 2934.5 cm$^{-1}$ represent $CH_2$ and $CH_3$, 1988.5 cm$^{-1}$ represents $NH_3^+$ isoform, 1621.5 cm$^{-1}$ represents C=O and 1541.5 cm$^{-1}$ represents deformation $NH_3^+$ (FIG. 3); and spectrum of pal-P-L-Lys, wherein 3280 cm$^{-1}$ and 1541.5 cm$^{-1}$ and other two peak associated with $NH_3^+$ do not exist, and comparison by using Spectroscopic tools available online from the University of Universität Potsdam (Potsdam, Germany) (http://www.science-and-fun.de/tools/) showed 3487 cm$^{-1}$, 3191 cm$^{-1}$ and 2781 cm$^{-1}$ might represents CONH, and 708 cm$^{-1}$ C–Cl represents not completely reacted portion of palmitoyl chloride, showing that pal-P-L-Lys was indeed synthesized (FIG. 4).

EXAMPLE 1

P300 DNA Decoy Recovers Cell Apoptosis Induced by Endotoxin

Accordingly, genes induced by APC contain P300 binding site. Sequence of P300 binding site was used as P300 DNA decoy to reduce effective concentration of intracellular P300 and β-catenin, whereby β-catenin was unable to transcribe its related genes, resulting in preventing cell apoptosis induced by endotoxin.

In the present example, pal-P-L-Lys-LDL was synthesized and a composition containing P300 DNA decoy was obtained by the methods as described in "General experimental methods", wherein P300 DNA decoy was a P300 binding sequence upstream coding sequence (CDS) of human TR3 orphan receptor mRNA transcriptionally regulated by P300. The sequence of P300 DNA decoy was TGGGGGAGTGCACA (SEQ ID NO.: 1), denoted as "P300". Mismatch sequence of "P300" was used as control and denoted as "mismatch P300, which was obtained by swapping position of TG in P300 to become (SEQ ID NO.: 2)
GTGGGGAGGTCACA.

As the method described in "4. Preparation of composition containing DNA decoy", introduction of P300 DNA decoy was then performed with carrier and includes: adding 1 mL of 100 ng/mL LPS to endothelial cells in 35 mm plate and incubating for 12 hours (n=3~9). The experimental groups were as indicated as X-axial in FIG. 5. The effect of P300 DNA decoy on cell apoptosis of endothelial cells stimulated with LPS was evaluated.

Figure 5:
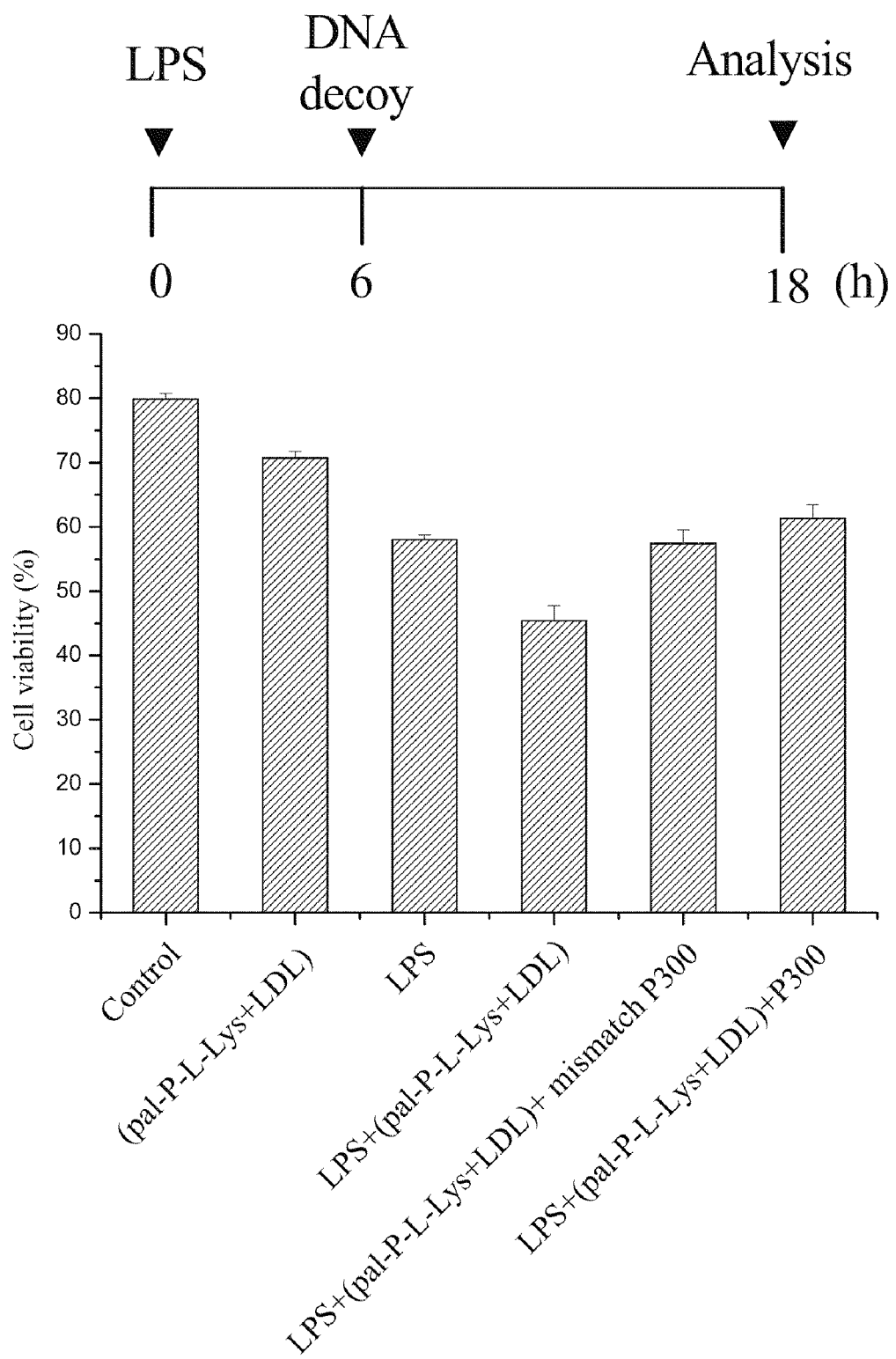
FIG. 5 illustrates effect of treatment of P300 DNA decoy on cell viability of endothelial cells stimulated with LPS.

As shown in FIG. 5, cell viability of cells treated with (pal-P-L-Lys)-LDL alone was reduced 10% compared to the control. This might result from effects of LDL on cells. When cells were subject to 6 hour-treatment of 100 ng/mL LPS in combination with addition of (pal-P-L-Lys)-LDL, cell viability was reduced to about 45%. When cells were subject to 6 hour-treatment of LPS and subsequent treatment of 3 μg (pal-P-L-Lys)-LDL-P300, cell viability was 3% higher than the group treated with LPS alone for 18 hours. The effect of P300 was slighter than APC, suggested that beyond binding to P300, β-catenin also associated with other proteins, including microphthalmia-associated transcription factor (MITF), to transcribe Bcl-2 related survival genes (J. Vachtenheim, B. Sestakova, and Z. Tuhackova, Pigment Cell Res., 2007, 20: 41-51). Therefore, once P300 cannot exert its function, other related functions were also hampered.

Recovering cells stimulated with LPS from apoptosis by P300 DNA decoy was much less effective than by APC, suggesting that APC exerts its function not only through P300 to reduce amount of available β-catenin in cell nucleus, but also through suppressing cell apoptosis associated genes.

EXAMPLE 2

TCF DNA Decoy Recovers Cell Apoptosis Induced by Endotoxin

In the present example, TCF-4 binding site upstream CDS of Cyclin D1 and Fra1 mRNA was used as TCF DNA decoy. One was selected from Cyclin D1 gene sequence by TRANSFAC database available online, having sequence of GGGCTTTGATCTTTGCTTAA (SEQ ID NO.: 3), denoted as "TCF-CyD1"; and the other was designed according to Fra1 gene sequence with reference to DNA binding sequence of TCF used by Mann et al. (B. Mann, et al., Proc. Natl. Acad. Sci. U.S.A., 1999, 96: 1603-1608), having sequence of AGAATCCCTTTAGCTCAGGA (SEQ ID NO.: 4), denoted as "TCF-Fra1". Furthermore, mismatch sequence of "TCF-Cyd1" was used as control, denoted as "mismatch TCF-CyD1". The sequence was obtained by swapping position of TG in TCF-4 binding site (TCF-CyD1) to become (SEQ ID NO.: 5)
GGGCTTGTATCTTGTCTTA.

Furthermore, as the methods described in the previous example, introduction of sample of each group was performed with carrier and includes: treating endothelial cells in 35 mm plate with 1 mL of 100 ng/mL LPS for 18 hours; at 6-hours after LPS treatment, further treating the endothelial cells with 3 μg TCF-4 DNA decoy (n=3~9); and evaluating cell viability of the endothelial cells. The experimental groups were indicated as X-axial in FIG. 6. The effect of TCF DNA decoy on cell apoptosis of endothelial cells stimulated with LPS was evaluated.

Figure 6:
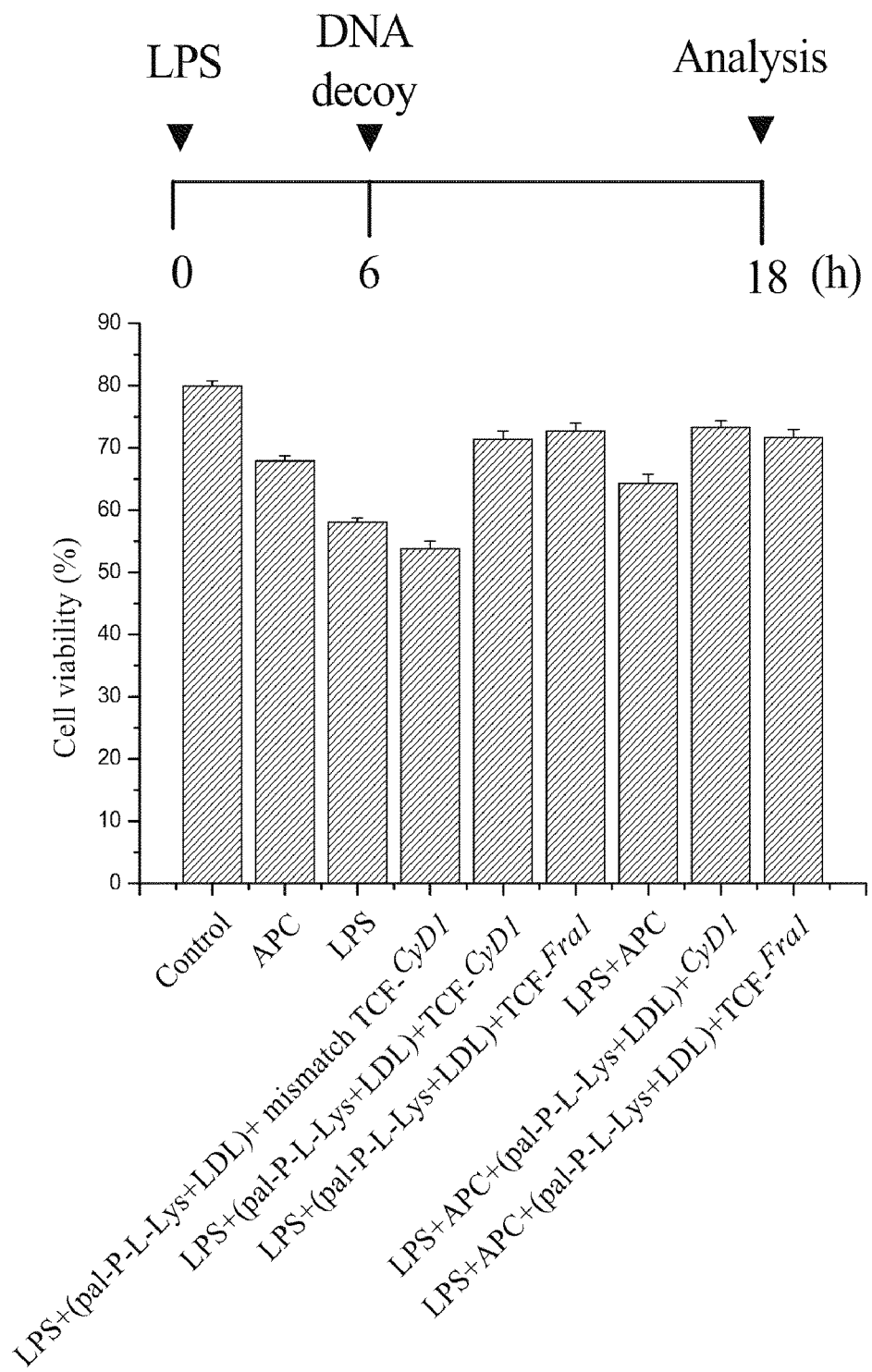
FIG. 6 illustrates effect of treatment of TCF DNA decoy on cell viability of endothelial cells stimulated with LPS.

As shown in FIG. 6, in the groups of cells was introduced with DNA decoy at 6 hours after 100 ng/mL LPS treatment, wherein cell viability of cells introduced with TCF DNA decoy derived from either CyclinD1 or Fra1 (TCF-CyD1 or TCF-Fra1) was increased to about 13% higher than the group of cells merely subject to 18-hour LPS treatment. In the group of cells treated with additional 70 ng/mL APC, cell viability was increased about 14%. The results indicated that TCF DNA decoy could increase cell viability of cells stimulated with LPS and addition of APC did not greatly alter increment of cell viability, indicating that use of DNA decoy could directly suppress function of TCF, which is superior to APC alone.

EXAMPLE 3

TCF DNA Decoy Influences No Release from Endothelial Cells

TCF DNA decoy increased cell viability of cells stimulated with LPS. Amount of NO release from endothelial cells was further evaluated in the present example. The present example was performed by the methods as described in the previous examples and the methods as described in "5. Measurement of nitric oxide" in "General experimental methods" to measure amount of released NO, which includes: adding DNA decoy to endothelial cells treated with 100 ng/mL LPS for 6 hours and incubating for 12 hours; and determining total amount of released NO in cells (n=2~3). The groups were as indicated as X-axial in FIG. 7.

Figure 7:
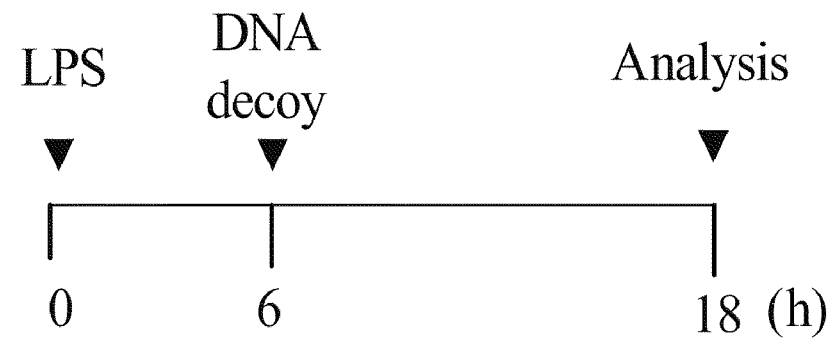
FIG. 7 illustrates effect of treatment of TCF DNA decoy on amount of released nitric oxide (NO) by endothelial cells stimulated with LPS.
Figure 7:
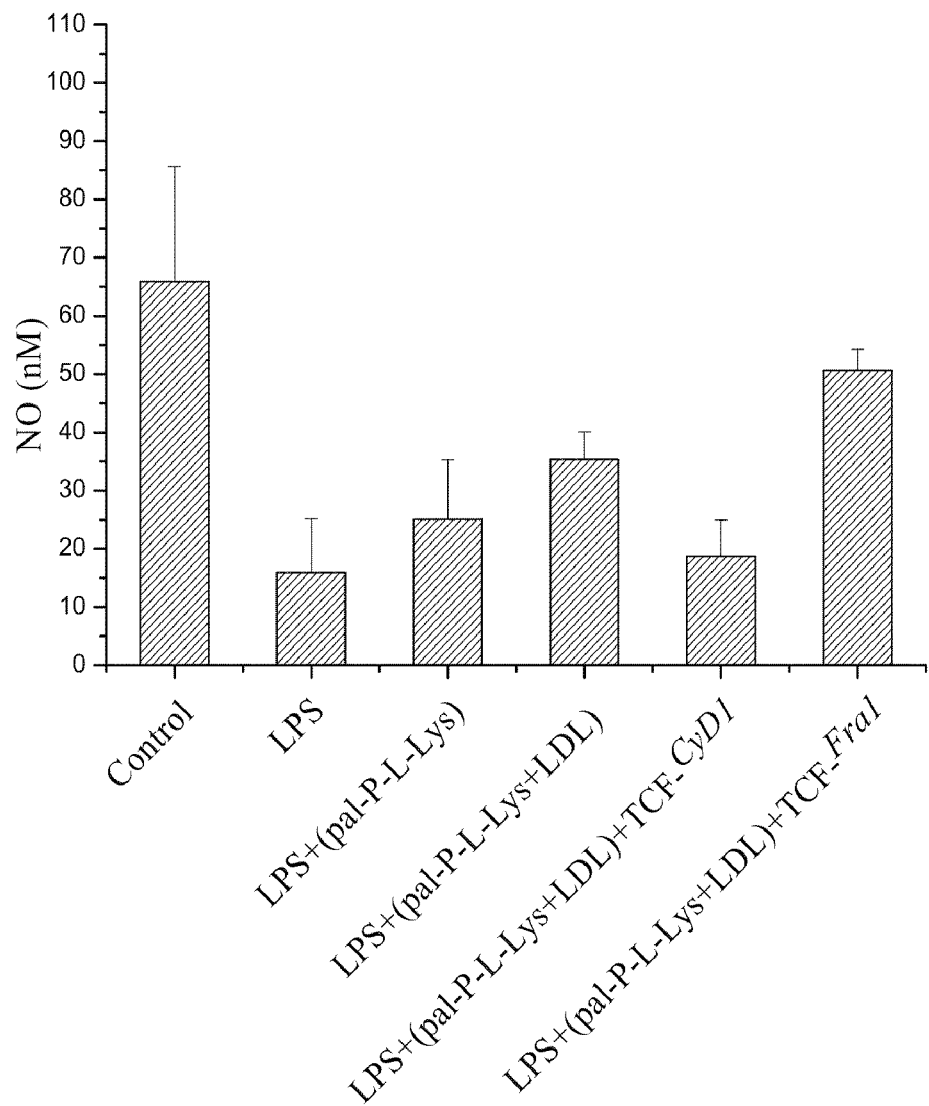

As shown by FIG. 7, in the group of cells treated with 100 ng/mL LPS alone for 18 hours, amount of released NO dramatically dropped. In the group of cells introduced with TCF DNA decoy after 6 hours, amount of released NO of cells was recovered by TCF DNA decoy derived from Fra1 at the 18th hour. Contrarily, effect of TCF DNA decoy derived from Cyclin D1 was less obvious. It was suggested that TCF DNA decoy derived from Cyclin D1 suppressed cell cycle, which led to lower NOS expression. Nevertheless, suppression of cell mobility by Fra1 could recover NOS expression.

Even though numerous characteristics and advantages of the present invention have been set forth in the foregoing description, together with details of the features of the invention, the disclosure is illustrative only. Changes may be made in the details within the principles of the invention to the full extent indicated by the broad general meaning of the terms in which the appended claims are expressed.

---

What is claimed is:

1. A method for alleviating cell apoptosis of endothelial cells induced by endotoxin, comprising:

administrating a pharmaceutical composition comprising a double-stranded TCF-4 DNA decoy oligonucleotide comprising the sequence of SEQ ID NO: 4 and a pharmaceutically acceptable carrier to endothelial cells stimulated by endotoxin, such that the cell apoptosis of the endothelial cells induced by endotoxin is decreased.

2. The method as claimed in claim 1, wherein the pharmaceutically acceptable carrier comprises palmitoyl poly-L-Lysine-low density lipoprotein (pal-P-L-Lys-LDL).

* * * * *